United States Patent [19]

Somers et al.

[11] Patent Number: 5,029,484
[45] Date of Patent: Jul. 9, 1991

[54] HAZARDOUS WASTE SAMPLER

[76] Inventors: Scott R. Somers, 77 Symons St., Richland, Wash. 99352; Gregory M. Somers, 1103 - 9th Ave., Milton, Wash. 98354

[21] Appl. No.: 463,325

[22] Filed: Jan. 10, 1990

[51] Int. Cl.⁵ .............................................. G01N 1/14
[52] U.S. Cl. ............................. 73/863.81; 73/863.83; 73/864.73
[58] Field of Search ........... 73/863.81, 863.83, 863.84, 73/864.73, 864.74, 864.62, 864.34

[56] References Cited

U.S. PATENT DOCUMENTS 2,158,803  5/1939  Renfro ............................. 73/863.83
3,813,945  6/1974  Crumal ....................... 73/864.34 X

FOREIGN PATENT DOCUMENTS 3424724  9/1985  Fed. Rep. of Germany ... 73/864.73
388213  10/1913  U.S.S.R. ............................. 73/863.83

OTHER PUBLICATIONS

"Disposable Glass Coliwasa, PACS"—*Environmental Sampling Equipment*, p. 69 (undated), but by Dec. 1989.
"The Geotech VACSAM Waste Sampling System", Specification Sheet Published by Geotech Environmental Equipment, Inc., Denver, Colo., (undated), (2 pages), but by Dec. 1989.

*Primary Examiner*—Tom Noland
*Attorney, Agent, or Firm*—Chernoff, Vilhauer, McClung & Stenzel

[57] ABSTRACT

A device and method for collecting a representative sample of hazardous fluid from a drum, and then disposing of the sampler, without ever removing the sampler from the drum so as to safeguard the operator from exposure to the hazardous fluid. The collected sample is moved, by a slidable plunger, along the inner channel of a hollow tube toward a drainage opening maintained at the top thereof while the bottom of the tube remains immersed within the tank. A break-apart construction of the sampler thereafter enables separation between its immersed and emergent portions, while the tube remains immersed, to safeguard the operator after sampling has been completed by enabling permanent disposal of the separated portions in the drum being sampled. An irreversible plunger movement feature discourages any attempt to reuse the sampler.

11 Claims, 3 Drawing Sheets

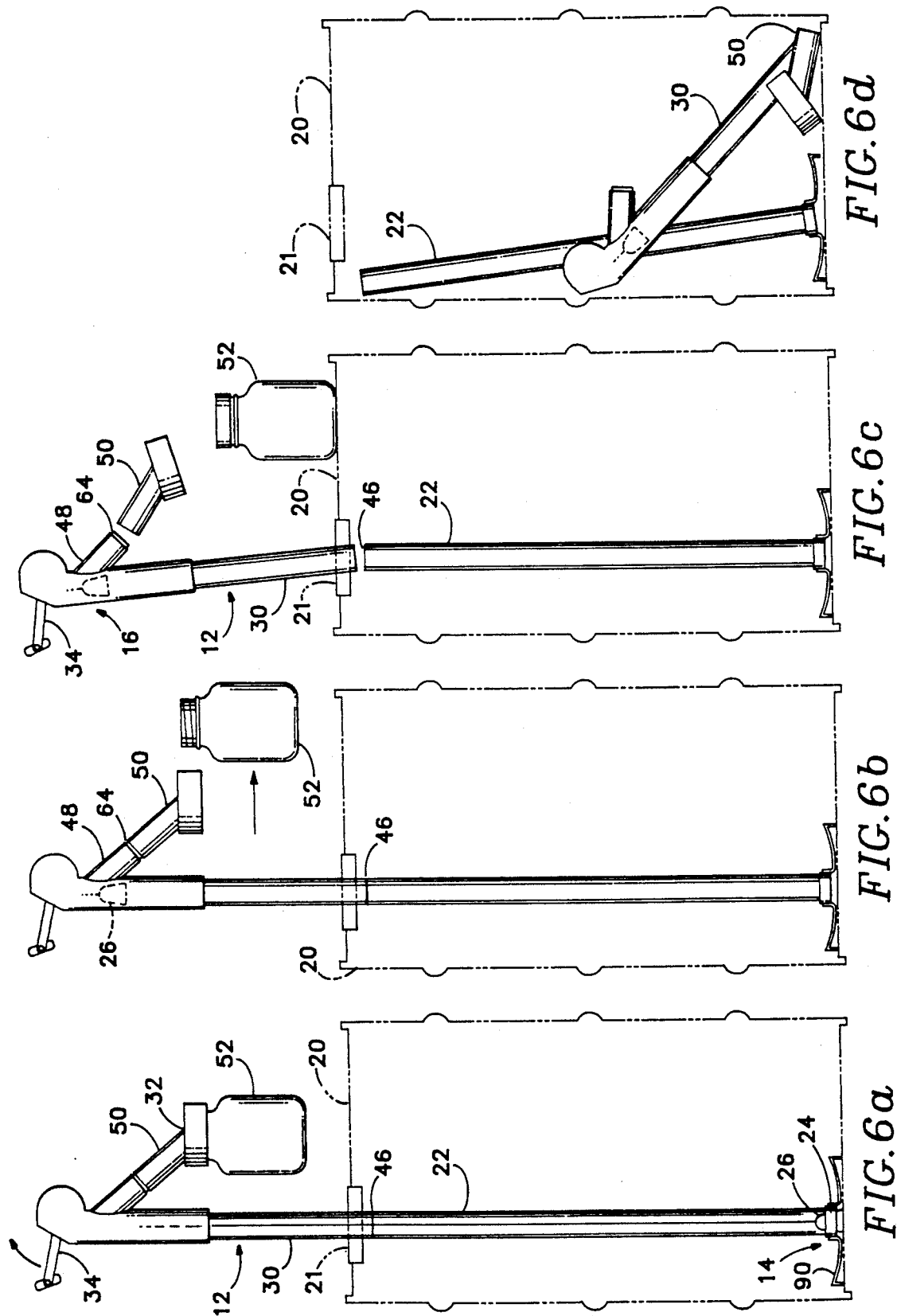

HAZARDOUS WASTE SAMPLER

BACKGROUND OF THE INVENTION

The present invention relates to a device for taking waste samples and, in particular, to such a device suitable for taking samples of hazardous waste fluid, such as toxic or radioactive fluid, from a drum or tank.

In the field of hazardous waste it is frequently necessary to determine the chemical composition of waste fluid contained in a drum or tank. Because of the stratification that often occurs in such fluids over time, it is necessary to sample each successive layer from the top to the bottom of the containing drum in order to obtain a sample accurately representative of the waste fluid contained therein. Accurate measurement of hazardous waste content is important, both to workers in the field and to the public, to prevent inappropriate handling, storage, or disposal that could endanger health. An additional concern affecting both measurement accuracy and safety is the adherence of amounts of hazardous material to the surfaces of the sampling device itself, leading to increased risk of harmful exposure to operators of the device during the sampling procedure, and to subsequent measurement errors due to cross contamination between the chemicals in separate drums.

One prior device designed for the sampling of hazardous fluid, developed by the Environmental Protection Agency and the State of California, is the Coliwasa or composite liquid waste sampler. Typically, the Coliwasa sampler comprises a hollow tube in which is disposed a rigid rod for controlling a valve in a fluid inlet at the bottom of the tube. After the hollow tube has been slowly lowered into the waste fluid with the inlet open, thereby permitting successive layers of waste fluid to collect inside the tube, the rigid rod is manipulated so that the inlet opening of the hollow tube is closed by the valve, whereupon the tube may be lifted out of the drum with the representative fluid column intact. The worker then repositions the tube over a collection vessel and opens the valve to discharge the fluid. The tube and rod of the sampler are both constructed of glass prescored to enable subsequent breakage and permanent disposal in the drum, thereby avoiding subsequent cross-contamination or the hazards of cleanup. However, during the sampling procedure there is a high likelihood of exposure to hazardous material because the operator is required to lift from the drum a long tube that is coated with hazardous material and from which hazardous material may drip and splash.

Another device suitable for sampling hazardous fluid from a tank is the VACSAM TM or vacuum-operated composite liquid sampler. This device is made by Geotech Environmental Equipment Incorporated of Denver, Colo. Like the Coliwasa, the VACSAM TM employs a hollow sampling tube, but relies on a vacuum pump to draw the fluid out of the top of the tube through flexible tubing into a collection bottle. Because the immersed portion of the tube remains in the drum during sampling, exposure of the operator to hazardous material is minimized. Furthermore, if the tube is constructed of scored glass, the tube may be broken while still immersed in the drum thereby permitting disposal of the tube, along with the flexible tubing, in the original drum being sampled. In the VACSAM TM device, however, the fluid from the bottom layers of a stratified fluid in the drum mixes with the representative sample through the bottom of the tube as the pump draws the representative sample upward, making the device susceptible to inaccuracies in sampling.

Additional sampling devices are disclosed in Renfro, U.S. Pat. No. 2,158,803 and Crumal, U.S. Pat. No. 3,813,945. While their features are of interest, these devices are not suitable for sampling hazardous fluids because their construction makes them difficult to decontaminate and because they are too expensive for disposal after a single sampling. In any case, the structures of these devices could not be disassembled for disposal without removing them from the fluid being sampled, thereby exposing their operators to the fluid.

What is required, then, is a hazardous waste sampler that both accurately collects a representative sample of a stratified fluid, and thereafter enables immediate disposal of the sampler in the drum from which the sample has been taken, all without ever requiring the removal of the immersed portion of the sampler from the drum, so as to avoid exposing the operator to the hazardous material sampled.

SUMMARY OF THE INVENTION

The present invention addresses the foregoing need, and thereby not only the safety concerns of operators but also the economic concerns of hazardous waste managers. A hollow tube sampler is provided having a lower immersible portion and an upper discharge portion. The representative sample enters an inlet at the bottom of the immersible portion, and is then sealed from the surrounding fluid by a plunger which is advanced upwardly through the tube to discharge the sample through the upper discharge portion while the immersible portion remains immersed in the fluid. After the plunger element has passed upwardly through the immersible portion of the tube, there are no further elements within the tube to connect the emergent discharge portion of the tube with the immersible portion. It becomes possible, therefore, to completely separate the discharge portion from the immersible portion while the immersible portion is maintained within the drum. This method prevents operator exposure after, as well as during, sampling of a particular drum. Furthermore, the separated discharge portion of the tube is adapted for disposal within the originally sampled drum.

A further inventive aspect of the present invention is a novel irreversible plunger movement feature which permanently prevents retraction of the plunger back down the tube, thereby discouraging any attempt to avoid permanent disposal of the sampler after use.

The foregoing and other features and advantages of the invention will be more readily understood upon consideration of the following detailed description of the invention, taken in conjunction with the accompanying drawings.

BRIEF DESCRIPTION OF THE DRAWINGS

FIGS. 6a-6d are sequential side views of the exemplary waste sampler during various stages of sampling and after sampling has been completed.

DESCRIPTION OF THE PREFERRED EMBODIMENT

Figure 1:
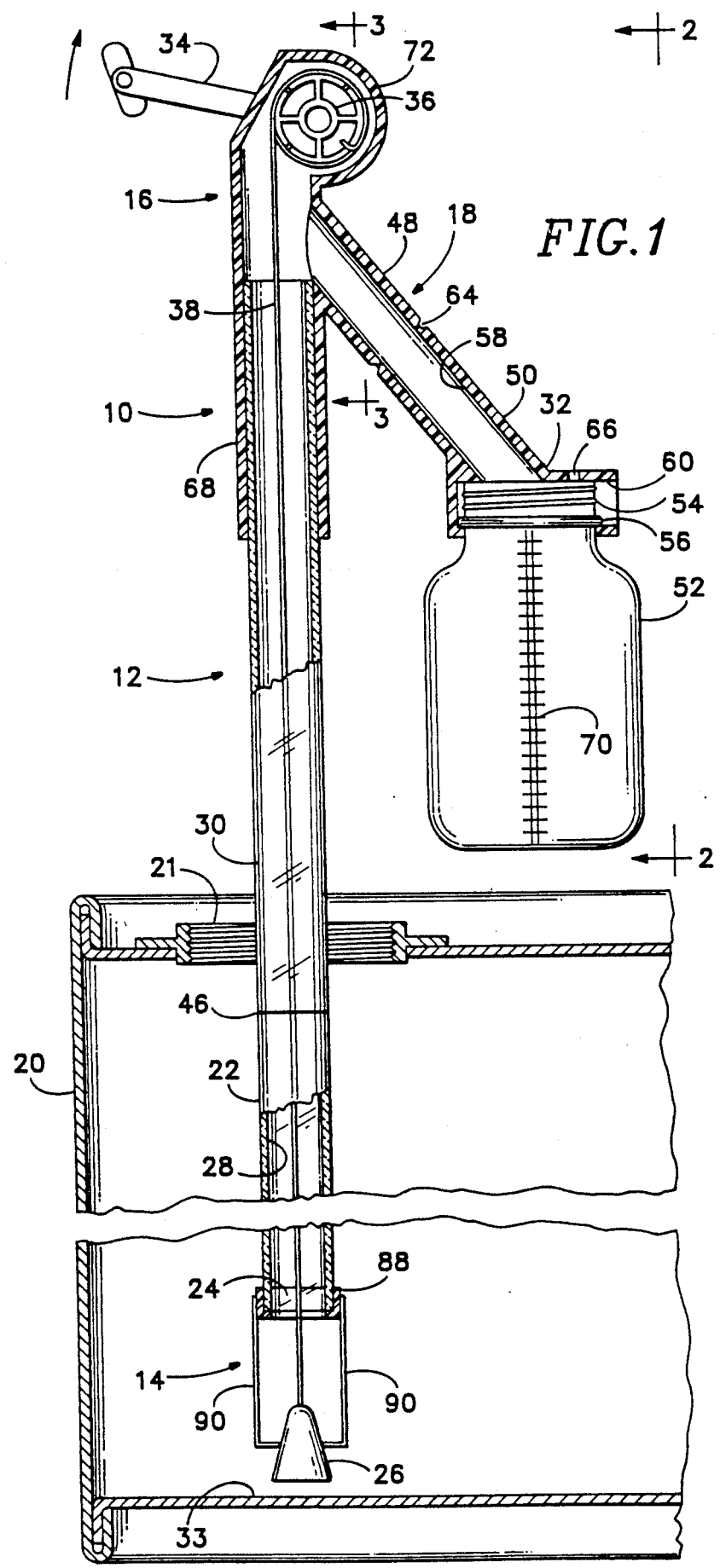
FIG. 1 is an extended side sectional view of an exemplary embodiment of a waste sampler, in accord with the present invention, disposed within a drum containing the hazardous fluid to be sampled.

FIG. 1 illustrates an exemplary embodiment of a waste sampler 10 constructed and operable in accordance with the present invention. The waste sampler 10 comprises an elongate hollow sampling tube 12, a plunger assembly 14, a plunger advancement assembly 16, and a drainage assembly 18. The waste sampler 10 is intended to be used for retrieving a sample of hazardous waste fluid from a conventional 55-gallon waste drum 20 or tank.

Use of the waste sampler requires the operator to position the sampling tube 12 over the bung opening 21 in the drum 20 and to gradually lower the tube 12 into the hazardous fluid contained therein. After the sampling tube 12 has made its descent through the fluid to the bottom of the drum 20, a column of the hazardous fluid will have collected in the immersible portion 22 of the sampling tube 12 by passage through the inlet opening 24 located at the bottom end thereof. With proper control of the rate of descent of the tube 12, the operator is able to collect a column of fluid representative of each stratified layer of fluid in proportionate amount to the thickness of each layer. Preferably, the hollow sampling tube 12 is made of transparent glass, for then the rate of descent may be visually controlled by maintaining the fluid column within the tube 12, during descent, at an even level with the top surface of the fluid outside of the tube.

After a representative column of fluid has been collected inside the tube 12, the inlet opening 24 of the tube 12 is sealed from the surrounding fluid by a plunger 26. Next, the plunger element 26, which is slidably and sealably engageable with the inner channel 28 of the tube 12, is drawn upward to discharge the representative sample from the immersible portion 22 of the tube, through the emergent discharge portion 30 of the tube, and out a drainage opening 32. More specifically, as explained in further detail below, the downward descent of the sampling tube 12 causes the plunger 26 to encounter the bottom surface 33 of the drum 20, whereupon the plunger element 26 is released into slidable engagement with the inner channel 28 at a location adjacent the inlet opening 24. While so engaged, the plunger element 26 serves as a barrier that isolates the representative fluid column inside the tube 12 from the remainder of the fluid contained in the drum 20. To slidably advance the plunger element 26 toward and through the discharge portion 30 of the tube 12, the operator actuates the plunger advancement assembly 16 by turning the detachable handle 34 in the direction shown in FIG. 1. This causes rotation of the take-up reel 36, subsequent winding of the flexible cable 38 around the take-up reel 36, and advancement of the plunger element 26 connected to flexible cable 38 upwardly away from the inlet opening 24 of the tube 12. When the plunger element 26 has attained sufficient height within the inner channel 28 of the tube 12, the representative sample will be drained from the tube 12 through the hollow drainage assembly 18 and out the drainage opening 32. The flexible cable 38 is preferably corrosion resistant and may be constructed of braided stainless steel wire or of flexible nonreactive synthetic wire of TEFLON TM or other suitable composition.

A major aspect of the present invention is the manner in which the immersible portion 22 of the sampling tube 12 may be maintained within the drum 20 not only while the sample is being taken as shown in FIGS. 6a and 6b, but also, as indicated by FIGS. 6c and 6d, after sampling has been completed and the device is being separated into pieces which are disposed of through the drum opening 21. At no time is it necessary for the operator to lift the immersible portion 22 of the tube 12 out of the drum 20. Such an action, if taken, would expose the operator to the hazardous material coating the immersible portion 22, which could brush off or splash onto the operator. The sampling tube 12 is preferably made of glass, and separation between the immersible portion 22 and discharge portion 30 of the tube 12 is facilitated by means of a peripheral scored groove 46 between the immersible portion 22 and discharge portion 30. By knocking the immersible portion of the glass tube against the inside of the drum, the tube will break at the scored groove 46 and separate the discharge portion 30 from the immersible portion 22.

Figure 2:
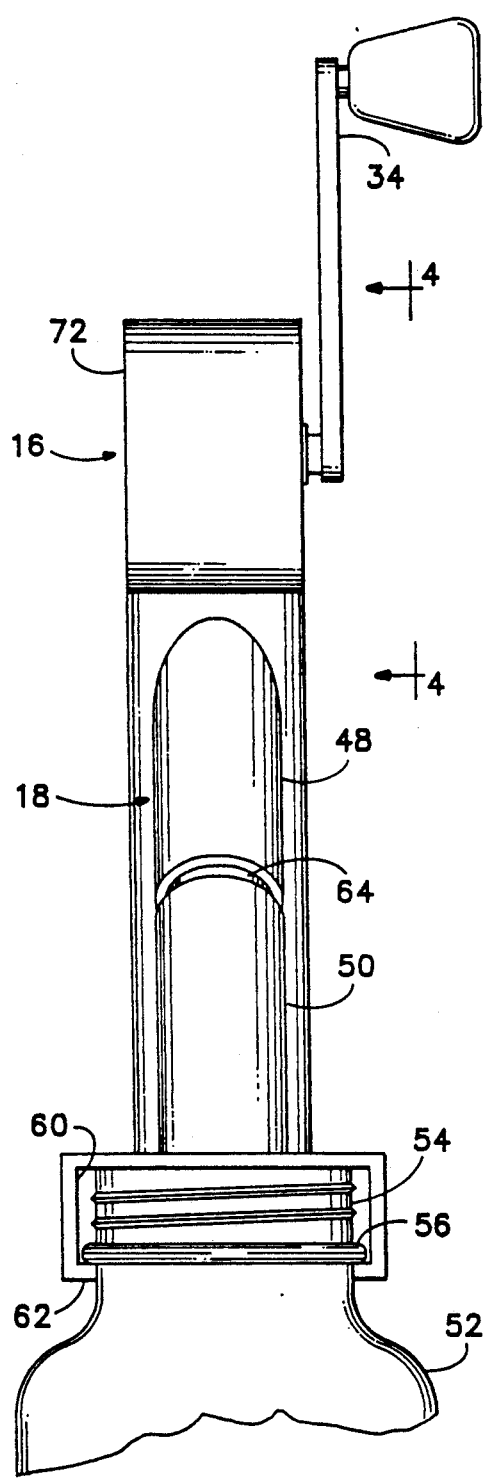
FIG. 2 is an enlarged front elevational view of the top portion of the exemplary waste sampler taken along line 2—2 of FIG. 1.

As indicated by FIGS. 6c and 6d, the exemplary invention permits, within the original drum 20, deposit not only of the immersible portion 22 of the tube 12 but also of the discharge portion 30. The discharge portion includes an exemplary drainage assembly 18 having an inclined plastic arm portion 48 and a splash guard portion 50. Connected at the lower end of the inclined arm portion 48, the hollow splash guard portion 50 serves to funnel the representative fluid sample into the collection vessel 52 without permitting spillage of the hazardous fluid over the threaded neck 54 and lip 56 of the vessel and without permitting splattering of the hazardous fluid onto the operator. It is preferable to provide a small vent hole 66 somewhat displaced from drainage opening 32 to prevent the buildup of air pressure that would otherwise occur during sampling were the reservoir to be entirely closed. The substantially closed construction of the discharge portion of the hazardous waste sampler 10, made possible by the exemplary drainage assembly 18, protects the operator from inadvertent contact with hazardous material while he or she handles the upper portions of the sampler. The collection vessel 52 is fitted into the open-ended receiving slot 60 of the splash guard portion 50 at any selected moment before discharge of the representative fluid sample from the drainage opening 32. Referring to FIGS. 1 and 2, movement of the collection vessel 52 in the direction indicated (FIG. 1) causes the lip 56 of the collection vessel to engage the shoulders 62 of the open-ended receiving slot 60 (FIG. 2). A peripheral groove 64 may be formed on the plastic drainage assembly 18 between the splash guard portion 50 and the inclined arm portion 48. Referring to FIGS. 6b and 6c, after sampling is complete and the collection vessel 52 has been removed from the splash guard portion 50, the splash guard portion 50 may be broken or twisted off at the groove 64 (FIG. 6c) and thereby uncoupled from the remainder of the discharge portion 30 of the tube 12. Referring to FIG. 6d, this allows the entire discharge portion 30, including the splash guard portion 50, to fit within the opening 21 of the sampled drum 20 for permanent deposit within the drum.

Preferably, the drainage assembly 18 is constructed of a stiff polymer having an inner surface 58 optionally coated with TEFLON ™ to prevent chemical interaction with the hazardous fluid sample. The drainage assembly 18 is provided with a neck 68 that is adhered, or otherwise coupled, to the sampling tube 12. Although the exemplary drainage assembly 18 is shown, by the drawings, as a multi-part member, it is within the broader conception of the present invention to have a drainage assembly 18 of simpler construction. For example, a drainage opening being defined in the top end of the discharge portion 30 of the sampling tube 12 would suffice. On the collection vessel 52, itself, it is preferable to make the volume of the vessel correspond to the volume of fluid in the tube 12 when the tube is immersed in a full drum, and to include indexing marks 70 that have been calibrated for the particular sized drum 20 being sampled. Because the volume of fluid contained in the tank correlates with the height of the fluid sample collected by the sampler 10, the indexing marks 70 may be used for gauging the volume of fluid contained in the tank.

Figure 3:
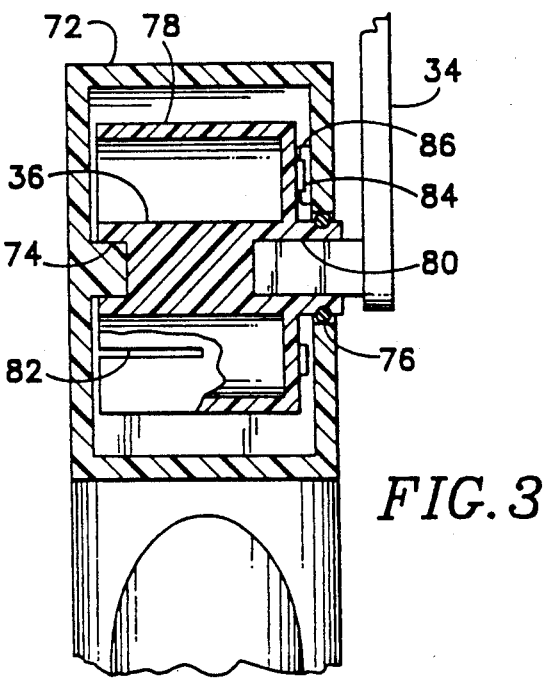
FIG. 3 is an enlarged front sectional view of the advancement mechanism of the selectively actuated plunger assembly taken along line 3—3 of FIG. 1.
Figure 4:
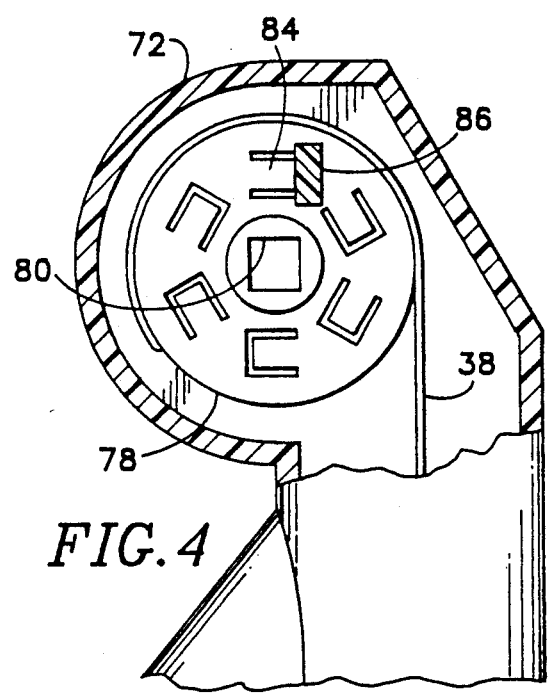
FIG. 4 is an enlarged side sectional view of the advancement mechanism of the selectively actuated plunger assembly taken along line 4—4 of FIG. 2.

The exemplary waste sampler 10 illustrated in FIG. 1 includes a selectively actuated plunger advancement assembly 16 comprising a flexible cable 38, a take-up reel 36 and a guard shield enclosure 72 mounted on the drainage assembly 18. Referring also to FIG. 3, take-up reel 36 is revolvably supported between an axle projection 74 and a sealed journal assembly 76 included on the guard shield enclosure 72. It will be recognized that the flexible cable 38, when taken up during sampling around the outer surface 78 of the take-up reel 36, includes a portion that has been immersed in hazardous material. The purpose of guard shield enclosure 72 is to provide a sealed shield around the outer surface 78 of the take-up reel 36 while still leaving a crank coupling 80 exposed so that the take-up reel 36 may be externally operated. This approach, unlike an approach relying on small stationary brushes to sweep an unenclosed cable as the cable is being wound, protects the operator from exposure to even trace amounts of hazardous material. As shown by FIG. 4, the crank coupling 80 may constitute a square hole in which may be fitted a detachable handle 34.

Figure 5:
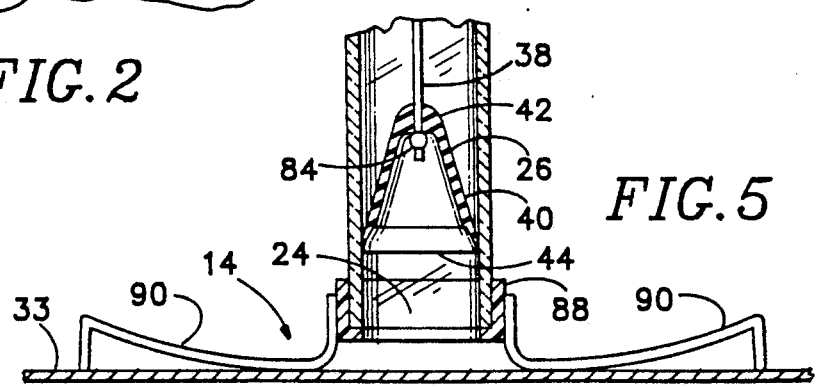
FIG. 5 is an enlarged sectional view of the lower portion of the plunger assembly.

During manufacture of the waste sampler 10, as shown by FIGS. 3 and 4, one end of the flexible cable 38 is fastened in a slot 82 in the outer surface 78 of the take-up reel 36 so that the flexible cable 38 is rotationally engageable therewith. The other end of the flexible cable 38, after being threaded through the sampling tube 12, is threaded, as shown by FIG. 5, through a hole in the hollow plunger element 26. Both ends of the cable are held by a knot or swaged bead 84.

During the sampling operation, the flexible cable 38 is irreversibly wound around outer surface 78 due to a non-releasable ratchet on the take-up reel 36. Referring to FIGS. 3 and 4, unwinding of the flexible cable 38 is prevented by flexible detents 84 molded into the side of the take-up reel 36 and by a non-releasable pawl 86 located on the guard shield enclosure. Besides discouraging any attempt to reuse the sampler which would cause cross-contamination, this ratchet also allows the operator to release the handle 34 while drawing the plunger upward and attend to other tasks without any risk of downward retraction of the plunger or the collected representative fluid sample. Even without the ratchet, however, re-use of the sampler would be effectively prevented by the fact that the flexible cable cannot push the plunger back down the tube in view of the plunger's frictional sealing contact with the interior of the tube, and no means are provided to pull the plunger down the tube.

As illustrated in FIGS. 1 and 5, the exemplary waste sampler 10 includes a plunger holding member 88 having opposed flexible arm clips 90 extending therefrom. As the sampling tube 12 is lowered into the hazardous fluid, the arm clips 90 hold the plunger element 26, between its rounded end 42 and flared end 44, away from the inlet opening 24 to allow passage of the hazardous fluid into the tube. After the plunger element 26 establishes contact with the bottom surface 33 of the drum 20, further downward pressure on the tube 12 causes the opposed arm clips 90 to slide downwardly along the plunger element toward the flared end 44 thereof until they eventually encounter the bottom surface of the drum 20, whereupon they continue to spread apart until they eventually break and assume their positions shown in FIG. 5. Once the opposed arm clips 90 have started to proceed across the bottom surface of the drum 20, the plunger element 26 freely rests on the bottom surface 33 of the drum in longitudinal alignment with the sampling tube 12, so that further downward motion of the sampling tube 12 causes the inlet opening 24 to become sealably engaged by the plunger element 26. In this manner, the sampling tube 10 collects a fluid column that is representative of even the bottommost fluid layers in the drum. The holding member 88 may either be pressure fitted, or glued, to the inlet opening 24, and preferably the member 88 and arm clips 90 are constructed of a 35 corrosion resistant material such as TEFLON ™.

FIGS. 6a–6d illustrate an exemplary method for collecting a representative sample of hazardous fluid from a drum by means of a device as depicted in the preceding figures. The sampling tube 12 is lowered into the hazardous fluid contained within the drum 20 at a proper rate for collecting a representative sample. The sampling tube 12 may be agitated slightly, while being lowered, to further ensure a representative mix from each stratified fluid layer in the drum. A point of initial resistance alerts the operator that the plunger has encountered the bottom surface of the drum 20, whereupon directly downward pressure is exerted on the sampling tube so that the arm clips 90 are brought to the position shown in FIG. 6a and so that the plunger element seals the inlet opening 24 of the sampling tube. This step isolates the representative fluid column within the tube from the remainder of the fluid contained within the drum. If not already engaged, the collection vessel 52 is now engaged within the splash guard portion 50 and the detachable handle 34 is turned in the direction shown. This causes the plunger element within the tube to raise the representative fluid column upwardly, through the emergent discharge portion 30, and out drainage opening 32 of the splash guard portion 50. Because the immersible portion 32 of the sampling tube 12 is maintained within the drum 20 throughout this procedure, at no time is the operator at risk of exposure to hazardous material.

After allowing time for all the hazardous fluid to drain from the splash guard portion 50, the collection vessel 52 is removed therefrom as shown in FIG. 6b. Referring to FIG. 6c, the operator applies a downward and transverse pressure on the sampling tube 12 to break the tube between the immersible portion 22 and discharge portion 30 at the scored groove 46 while the immersible portion 30 remains disposed within the tank. At this point, the opening 21 of the drum 20 could then be sealed and the discharge portion disposed of elsewhere. Preferably, however, breakdown of the device is continued with the separation of splash guard portion 50 from inclined arm portion 48 and the removal of detachable handle 34. Referring to FIG. 6d, each of the separated parts may then be fit through the opening 21 in the drum 20, and the opening then sealed, to achieve permanent disposal of the separable parts of the device within the drum.

It will therefore be appreciated that the aforementioned advantages have been achieved. The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method for removing, through an opening in a tank, a representative sample of fluid contained in the tank, said method comprising the following steps.
   (a) immersing an immersible portion of a hollow tube generally vertically in the fluid so that a representative sample of the fluid is collected within said tube through an inlet opening near the lower end thereof;
   (b) discharging the representative sample of the fluid from the tube, while maintaining said immersible portion within the tank, by moving a plunger from said inlet opening along the interior of the tube thereby conducting said sample toward an upper discharge portion of the tube and out a drainage opening; and
   (c) thereafter separating the discharge portion of the tube from the immersible portion of the tube while the immersible portion remains within the tank so as to dispose of the immersible portion in the tank.

2. The method of claim 1, further comprising the step, after step (c), of disposing of the discharge portion of the tube within the tank.

3. The method of claim 2, further comprising disassembling said discharge portion into multiple pieces prior to disposing of it within the tank.

4. The method of claim 1, further comprising the step of coupling the open end of a collection vessel to said drainage opening before discharging the sample therefrom.

5. The method of claim 4, further comprising, after discharging the sample from the drainage opening, the additional steps of uncoupling the open end of the collection vessel from the drainage opening, uncoupling the drainage opening from the remainder of the discharge portion of the tube, and disposing of the drainage opening and remainder of the discharge portion of the tube within the tank.

6. The method of claim 4, further comprising the step of gauging the volume of fluid contained in the tank by inspecting indexing marks on a side of the collection vessel.

7. A sampling device for removing, through an opening in a tank, a representative sample of fluid contained in the tank, said sampling device comprising:
   (a) an elongate hollow tube having an inner channel defined therein, said tube including an immersible portion having an inlet end and a discharge portion;
   (b) inlet means, proximate said inlet end of said immersible portion of said tube, for permitting access to said inner channel so that a representative sample of the fluid may be collected within said inner channel as said immersible portion is lowered into the fluid;
   (c) said discharge portion including drainage means, for permitting drainage of said representative sample of the fluid from said inner channel outside of the opening in the tank, while said immersible portion is maintained within the tank;
   (d) selectively actuated plunger means coupled to the discharge portion of said tube, including a plunger element sealably engageable with said inner channel of said tube and movable with respect to said inner channel from said inlet means toward said discharge portion of said tube, for conducting said sample along said inner channel toward said drainage means for drainage of said sample therefrom; and
   (e) disassembly means for enabling the separation of said discharge portion of said tube from said immersible portion thereof while said immersible portion is maintained within the tank, and for enabling the disposal of said discharge portion within said tank.

8. A sampling device as recited in claim 7 wherein said disassembly means includes a peripheral groove defined in said tube between said immersible portion and said discharge portion.

9. A sampling device as recited in claim 7 wherein said drainage means includes coupling means for detachably matingly coupling to a collection vessel.

10. A sampling device as recited in claim 9 wherein said disassembly means includes separation means for separating said coupling means from the remainder of said discharge portion.

11. A sampling device as recited in claim 10 wherein said separation means includes a groove defined in said drainage means between said coupling means and the remainder of said discharge portion.

* * * * *

UNITED STATES PATENT AND TRADEMARK OFFICE
CERTIFICATE OF CORRECTION

PATENT NO. : 5,029,484

DATED : July 9, 1991

INVENTOR(S) : Scott R. Somers et al.

It is certified that error appears in the above-identified patent and that said Letters Patent is hereby corrected as shown below:

Col. 3, line 33   After "control" delete "."

Col. 4, line 22   After "between" delete "-"

Col. 6, line 35   After "a" delete "35"

Col. 7, line 27   After "steps" change "." to --:--

Signed and Sealed this

Ninth Day of February, 1993

Attest:

STEPHEN G. KUNIN

Attesting Officer

Acting Commissioner of Patents and Trademarks